(12) United States Patent
Ishii et al.

(10) Patent No.: US 10,333,280 B2
(45) Date of Patent: Jun. 25, 2019

(54) SEMICONDUCTOR LASER DEVICE

(71) Applicants: Nippon Telegraph and Telephone Corporation, Tokyo (JP); Tohoku University, Miyagi (JP)

(72) Inventors: Hiroyuki Ishii, Atsugi (JP); Naoki Fujiwara, Atsugi (JP); Kei Watanabe, Atsugi (JP); Mikitaka Itoh, Atsugi (JP); Keisuke Kasai, Sendai (JP); Masataka Nakazawa, Sendai (JP)

(73) Assignees: Nippon Telegraph and Telephone Corporation, Tokyo (JP); Tohoku University, Miyagi (JP)

( * ) Notice: Subject to any disclaimer, the term of this patent is extended or adjusted under 35 U.S.C. 154(b) by 0 days.

(21) Appl. No.: 15/762,003

(22) PCT Filed: Sep. 29, 2016

(86) PCT No.: PCT/JP2016/004396
§ 371 (c)(1),
(2) Date: Mar. 21, 2018

(87) PCT Pub. No.: WO2017/056499
PCT Pub. Date: Apr. 6, 2017

(65) Prior Publication Data
US 2018/0269659 A1    Sep. 20, 2018

(30) Foreign Application Priority Data
Sep. 29, 2015   (JP) .................................. 2015-192106

(51) Int. Cl.
*H01S 5/40*   (2006.01)
*G02B 6/42*   (2006.01)
(Continued)

(52) U.S. Cl.
CPC ........... *H01S 5/4087* (2013.01); *G01N 21/01* (2013.01); *G02B 6/12* (2013.01); *G02B 6/42* (2013.01);
(Continued)

(58) Field of Classification Search
CPC . H01S 5/12; H01S 5/141; H01S 5/146; H01S 5/147; H01S 5/4087; H01S 5/0265;
(Continued)

(56) References Cited

U.S. PATENT DOCUMENTS 9,203,212 B2 * 12/2015 Kurobe ..................... H01S 5/50
2010/0014865 A1 * 1/2010 Sorin .................... H04B 10/506
398/79
2012/0163821 A1   6/2012 Kwon et al.

FOREIGN PATENT DOCUMENTS

JP      64-46995 A      2/1989
JP      H9-246642 A     9/1997
(Continued)

OTHER PUBLICATIONS

International Search Report dated Dec. 20, 2016, issued in PCT Application No. PCT/JP2016/004396, filed Sep. 29, 2016.
(Continued)

*Primary Examiner* — Tod T Van Roy
(74) *Attorney, Agent, or Firm* — Workman Nydegger

(57) ABSTRACT

A configuration of a DFB laser-based wavelength tunable laser is well known, but long resonators have difficulty in forming uniform resonators due to production variations, thereby inducing limitation in narrowing the spectral linewidth in the DFB laser-based wavelength tunable laser as well. In the semiconductor laser device of the present invention, a semiconductor laser that oscillates in a single mode and a low-loss lightwave circuit using $SiO_2$ glass are arranged on the common substrate. The lightwave circuit is
(Continued)

configured such that part of output light from the semiconductor laser propagates through a certain length of an optical path, and then is reflected by a reflector and is fed back to the semiconductor laser. Output light from the semiconductor laser and an input waveguide of the lightwave circuit can also be configured to be optically connected directly to each other. The present invention can provide a compact laser device with a narrowed spectral linewidth and stable wavelength controllability.

15 Claims, 8 Drawing Sheets

(51) Int. Cl.
  *G01N 21/01* (2006.01)
  *G02B 6/12* (2006.01)
  *H01S 5/022* (2006.01)
  *H01S 5/026* (2006.01)
  *H01S 5/12* (2006.01)
  *H01S 5/125* (2006.01)
  *H01S 5/50* (2006.01)
  *H01S 5/02* (2006.01)
  *H01S 5/0683* (2006.01)
  *H01S 5/14* (2006.01)
  *H01S 5/30* (2006.01)
  *H01S 5/024* (2006.01)
  *H01S 5/028* (2006.01)
  *H01S 5/10* (2006.01)

(52) U.S. Cl.
  CPC .............. *H01S 5/022* (2013.01); *H01S 5/026* (2013.01); *H01S 5/0206* (2013.01); *H01S 5/02252* (2013.01); *H01S 5/02284* (2013.01); *H01S 5/06835* (2013.01); *H01S 5/12* (2013.01); *H01S 5/125* (2013.01); *H01S 5/14* (2013.01); *H01S 5/3013* (2013.01); *H01S 5/50* (2013.01); *H01S 5/0287* (2013.01); *H01S 5/02288* (2013.01); *H01S 5/02415* (2013.01); *H01S 5/02492* (2013.01); *H01S 5/1039* (2013.01)

(58) Field of Classification Search
  CPC ... H01S 5/026–0268; H01S 5/40–4093; H01S 5/1021
  See application file for complete search history.

(56) References Cited

FOREIGN PATENT DOCUMENTS

| JP | 2007-94336 A | 4/2007 |
| JP | 2011-198903 A | 10/2011 |
| JP | 2014-135351 A | 7/2015 |
| JP | 2016-152253 A | 8/2016 |

OTHER PUBLICATIONS

International Preliminary Report on Patentability and Written Opinion dated Apr. 12, 2018, issued in PCT Application No. PCT/JP2016/004396, filed Sep. 29, 2016.

Marc Finot et al., *Thermally Tuned External Cavity Laser with Micromachined Silicon Etalons: Design, Process and Reliability*, 2004 Electronic Components and Technology Conference, 2004, pp. 818-823.

Klaus Petermann, *External Optical Feedback Phenomena in Semiconductor Lasers*, IEEE Journal of Selected Topics in Quantum Electronics, vol. 1, No. 2, Jun. 1995, pp. 480-489.

\* cited by examiner

SEMICONDUCTOR LASER DEVICE

TECHNICAL FIELD

The present invention relates to a semiconductor laser light source, and, more particularly, to the semiconductor laser light source, or a semiconductor laser device, which operates in a single mode used for mid- and long-distance optical fiber communications and optical sensing for gas and the like.

BACKGROUND ART

Recently, along with the increase of the capacity of an optical communication system, a digital coherent communication scheme using multivalued phase amplitude modulation has become increasingly popular. This communication scheme is a scheme to transfer a digital signal using optical phase information, and thus, a laser light source with less phase noise and a narrower spectral linewidth is required for a light source from which carrier light is supplied.

There are various kinds of laser light sources, but since a semiconductor laser is compact and of low cost, it has become widespread as a light source for optical communications. In particular, in a mid- and long-distance optical communication system, a Distributed FeedBack type (DFB) laser and the like which operate in a single mode is widely used. Further, in the mid- and long-distance optical communication system, Wavelength Division Multiplexing (WDM) technology is generally used for increasing the capacity of transfer per optical fiber. Therefore, a wavelength tunable characteristic capable of outputting an arbitrary wavelength channel is also required for the light source for making digital coherent communications.

Since the semiconductor laser has a resonator of a small size compared to other types such as a solid-state laser and a gas laser, its phase noise is relatively large. For example, a linewidth of the semiconductor laser having the general resonator size of several hundreds of μm is in MHz order. Here, the linewidth refers to a spectral linewidth, and is represented in Full Width at Half Maximum (FWHM) of a spectrum. In a digital coherent communication system of 100 Gbit/s which has presently been widespread, a Quadrature Phase Shift Keying (QPSK) modulation scheme is used, and a spectral linewidth of several hundreds of kHz is required for the laser light source. For such a purpose, a wavelength tunable DFB laser array and an external cavity type laser having a resonator length extended to about 1 mm so as to narrow the spectral linewidth, for example, are used. For realizing large volume of communications by using a modulation scheme with a greater multivalued degree, it is expected that the light source of a further narrower spectral linewidth will be implemented in future. In addition, also for application to optical sensing other than the communications, the light source of a narrower spectral linewidth is required to observe a narrow absorption line spectrum with high sensitivity.

CITATION LIST

Non Patent Literature
M. Finot, et al., "Thermally tuned external cavity laser with micromachined silicon etalons: design, process and reliability," Electronic Components and Technology Conference 2004 Proceedings, Vol. 1, pp. 818-823, 2004

(Non Patent Literature 2)
K. Petermann, "External optical feedback phenomena in semiconductor lasers," IEEE J. Quantum Electron., vol. 1, No. 2, pp. 480-489, 1995

SUMMARY OF INVENTION

Technical Problem

As a laser that can narrow the spectral linewidth in a semiconductor laser to about 10 kHz, there is a so-called external cavity type laser which is composed of an optical resonator outside a semiconductor chip. For example, NPL 1 discloses an external cavity type laser composed of a semiconductor optical amplifier, an external reflector, an etalon filter for choosing wavelengths, lenses, and the like. Due to this configuration, a wavelength tunable characteristic covering the entire C-band of 1550 nm and a linewidth characteristic having several tens of kHz are reported to be obtained. However, the external cavity type laser requires multiple components other than the semiconductor chip, and there has been necessity to assemble them with higher precision. Further, in the external cavity type laser, at least two or more wavelength filters must be controlled for choosing one wavelength among multiple resonance modes, thereby inducing a problem that their control circuits are complicated. Moreover, in the manufacturing process of semiconductor laser devices, a complicated testing and inspection on wavelength characteristics has been another problem.

As another configuration for narrowing the spectral linewidth, a wavelength tunable laser using a DFB laser is also known. In this configuration, a wavelength can be changed by using temperature control while rationally keeping the same oscillation mode. For this reason, a control for tuning wavelengths is simple. By extending the length of a resonator to about 1 mm, the DFB laser-based wavelength tunable laser can obtain the linewidth of up to about 100 kHz. However, if the resonator is to be further elongated, it would be difficult to maintain uniformity of diffraction grating pitches and uniformity of the equivalent refractive indexes of optical waveguides constituting the resonator. Therefore, in long resonators, it is difficult to form uniform resonators due to production variations, thereby inducing limitation in narrowing the spectral linewidth in the DFB laser-based wavelength tunable laser as well.

It is known that, by feeding back part of oscillation light of the semiconductor laser from the outside, the effect of narrowing the spectral linewidth can be obtained. For example, NPL 2 discloses a configuration of feeding light back to a semiconductor laser using an optical fiber. According to the configuration of NPL 2, by feeding part of light back to the semiconductor laser from the outside, the spectral linewidth can be narrowed by two digits or more. However, in a method of using optical fibers, there has been difficulty in stabilizing oscillations. The oscillating state of the semiconductor laser is sensitive to the phase of feedback light, and when the phase state of feedback light changes, wavelength hopping or the like due to an external cavity mode has been occurred. In other words, in the configuration of feedback type using an optical fiber, the oscillating state against subtle changes such as displacement, stress, and temperature of the optical fiber becomes unstable, and thus, it has been difficult to use it as a wavelength tunable light source in the environment of an actual communication device.

An object of the present invention is to realize, in consideration of the above problems, the light source which is composed of a semiconductor laser, which is compact and has good controllability, and which has a narrowed spectral linewidth.

Solution to Problem

One aspect of the present invention is a semiconductor laser device comprising: a first substrate having a semiconductor laser formed thereon which oscillates in a single mode; a second substrate having a lightwave circuit formed thereon which is configured to propagate part of output light from the semiconductor laser through a fixed length of an optical path and then to feed it back to the semiconductor laser; and a third substrate having the first substrate and the second substrate mounted thereon, wherein output light from the semiconductor laser on the first substrate and an input waveguide of the lightwave circuit on the second substrate are optically connected to each other.

Preferably, the lightwave circuit on the second substrate may include a reflector which reflects the propagated light and may be configured such that light reflected by the reflector is fed back to the semiconductor laser.

Further, the lightwave circuit on the second substrate may include branching means for branching the output light from the semiconductor laser to generate the part of the output light. In addition, the first substrate may also include: branching means for branching the output light from the semiconductor laser into two, and generating the part of the output light of the second substrate as one branched light and generating output light of the semiconductor laser device as another branched light; and a first semiconductor optical amplifier that amplifies the one branched light of the branching means and a second semiconductor optical amplifier that amplifies the other branched light of the branching means.

Preferably, the output light from the semiconductor laser on the first substrate and the input waveguide of the lightwave circuit on the second substrate may be coupled between an end face of the first substrate and an end face of the second substrate that faces the end face of the first substrate.

The semiconductor laser may be a distributed feedback type (DFB) laser or a distributed reflection type (DBR) laser which includes a wavelength selective function by a diffraction grating. Also, preferably, the semiconductor laser may include a number N of distributed feedback type (DFB) laser arrays, an optical multiplexer configured so as to multiplex each of output lights from the number N of DFB laser arrays, and a semiconductor optical amplifier, all integrated therein, and may operate as a wavelength tunable laser. Alternatively, the semiconductor laser may also include a number N of distributed reflection type (DBR) laser arrays, an optical multiplexer configured so as to multiplex each of output lights from the number N of DBR laser arrays, and a semiconductor optical amplifier, all integrated therein, and may also operate as a wavelength tunable laser. The above-described optical multiplexer may be configured as an N-to-one optical multiplexer, or may be configured as an N-to-two optical multi/demultiplexer.

Advantageous Effects of Invention

According to the present invention, operation with a narrowed spectral linewidth can be made by returning the part of the output light of the semiconductor laser to the semiconductor laser by using a lightwave circuit for optical feedback. The light source which is configured by the combination of a semiconductor laser chip and a lightwave circuit chip, which is compact and has good controllability, and which has a narrowed spectral linewidth is realized.

DESCRIPTION OF EMBODIMENTS

In a semiconductor laser light source of the present invention, operation with a narrowed spectral linewidth can be made by returning part of output light of a semiconductor laser to the semiconductor laser by using a lightwave circuit for optical feedback. As described above, in the configuration of feeding light back to the semiconductor laser using an optical fiber, as in NPL 2, the oscillating state against subtle changes such as displacement, stress, and temperature of the optical fiber becomes unstable, and thus, it has been difficult to use it in the environment of an actual communication device.

In contrast, in the semiconductor laser device of the present invention, an optical-feedback lightwave circuit is configured by using an optical waveguide free from deformation, and simultaneously, a substrate including the lightwave circuit and a substrate having the semiconductor laser held thereon are arranged on the same substrate. Due to this, it is possible to ensure stability of an operation environment of an optical feedback circuit. Further, in the configuration of the optical feedback of the semiconductor laser device of the present invention, the lightwave circuit does not include a function of a wavelength selective filter, but a wavelength tunable function included in the semiconductor laser is used. Due to this, as in the configuration of the external cavity laser, it is an advantage that there is no need to make precise adjustment of wavelengths of a filter. As such, in the configuration of the semiconductor laser device of the present invention, the light source which is small and stable, which has good wavelength controllability, and which has a narrowed spectral linewidth can be realized. Incidentally, in the following explanation, the semiconductor laser light source and the semiconductor laser device, as described herein, have the same meaning. With reference to the drawings, various embodiments of the present invention will be explained below.

First Embodiment

Figure 1:
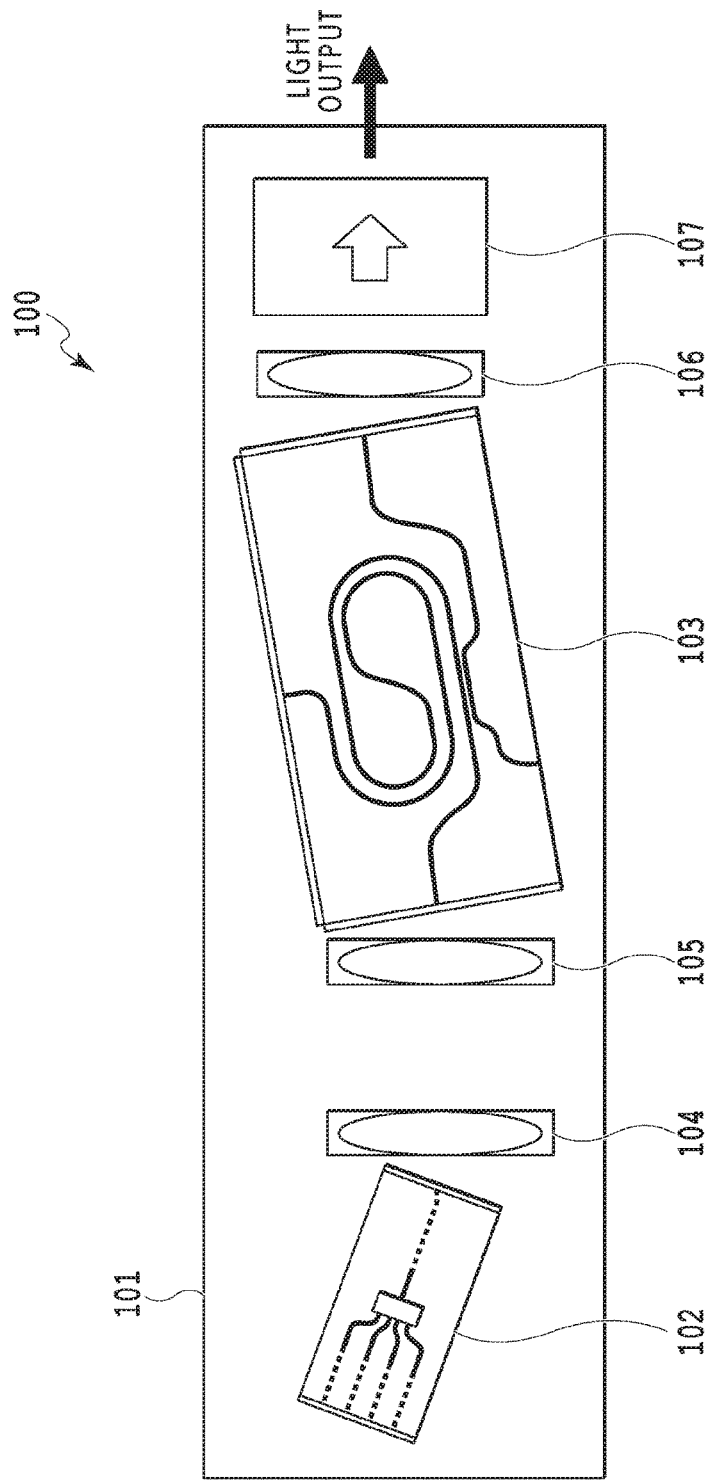
FIG. 1 is a diagram showing a rough sketch of a semiconductor laser device according to a first embodiment of the present invention.

FIG. 1 is a diagram showing a rough sketch of a semiconductor laser device according to the first embodiment of the present invention. A semiconductor laser device 100 of the present embodiment includes a wavelength tunable semiconductor laser chip 102 and an optical-feedback lightwave circuit chip 103 which are mounted on a single substrate 101. On an output end side of the wavelength tunable semiconductor laser chip 102, lenses 104, 105 are arranged such that output light enters into an input waveguide of the lightwave circuit chip 103. As a material for the substrate 101, a metal material such as a tungsten-copper alloy (CuW) having good thermal conductivity is used. Although not depicted in FIG. 1, a Thermo-Electric Cooler (TEC) is disposed at the back side of the substrate 101 to control the overall temperature of the substrate 101.

Output light emitted from the wavelength tunable semiconductor laser chip 102 is firstly converted into a collimated beam by the lens 104 and the light is concentrated to the input waveguide of the lightwave circuit chip by the lens 105. As will be described later, part of light output from the wavelength tunable semiconductor laser chip 102 is configured to return by reflection from the lightwave circuit 103. This reflected light travels along an optical path opposite to an outward route to the lightwave circuit 103, and is fed back to an output waveguide of the wavelength tunable semiconductor laser chip. Inside the lightwave circuit 103, light other than the feedback light is guided to the output waveguide as output light. The output light emitted from the lightwave circuit 103 is converted into a collimated beam by a lens 106 and is used as output light of the semiconductor laser device through an optical isolator 107. The optical isolator 107 is used to prevent laser oscillations from being unstable due to light returned from the outside of the semiconductor laser device. In the case of guiding light to the optical fiber, the collimated beam after passing the isolator may be input into the optical fiber by using a condensing lens.

Figure 2A:
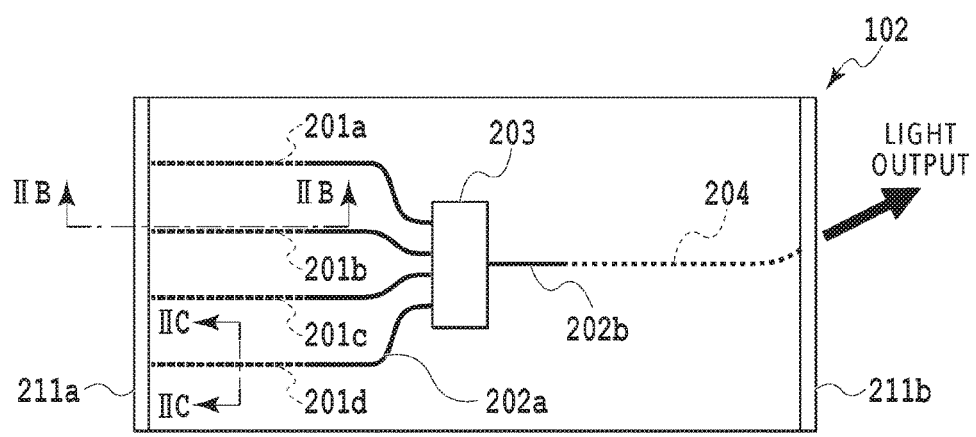
FIG. 2A is a top view showing a more specific structure of a wavelength tunable semiconductor laser chip of the semiconductor laser device of the present invention.
Figure 2B:
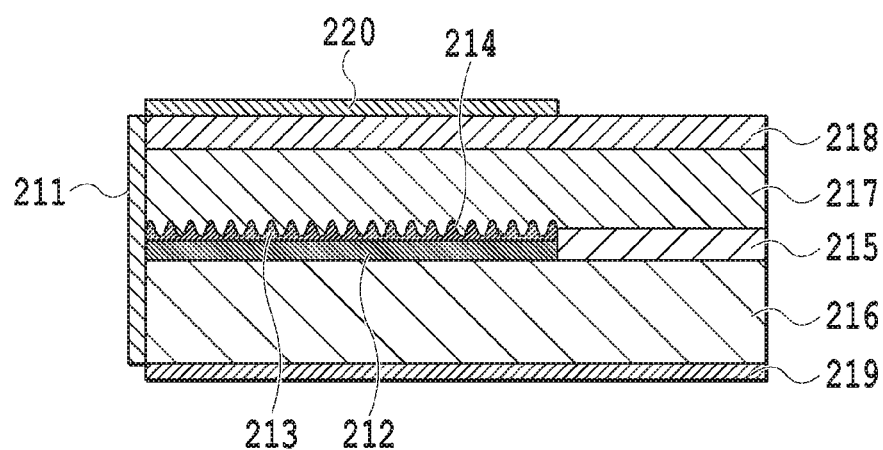
FIG. 2B is a cross-sectional view along the longitudinal direction of an oscillator of the wavelength tunable semiconductor laser chip for the semiconductor laser device of the present invention.
Figure 2C:
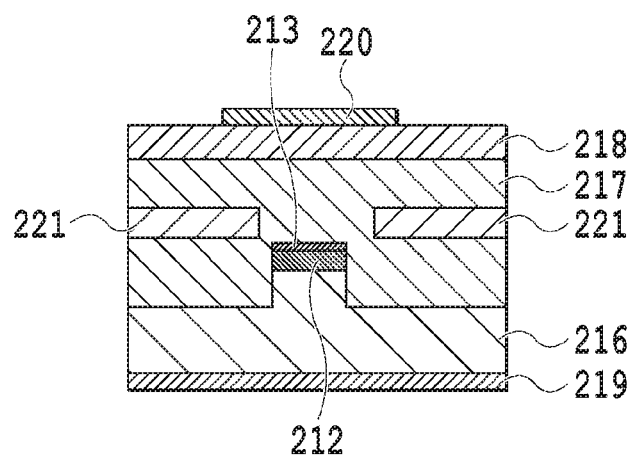
FIG. 2C is a cross-sectional view which is vertical to the longitudinal direction of the oscillator of the wavelength tunable semiconductor laser chip for the semiconductor laser device of the present invention.

FIG. 2A to FIG. 2C are diagrams showing a more specific structure of the wavelength tunable semiconductor laser chip of the semiconductor laser device of the present invention. FIG. 2A is a top view viewing the substrate face of the wavelength tunable semiconductor laser chip 102. FIG. 2B is a cross-sectional view as viewed by cutting vertically with respect to the substrate face in line IIB-IIB of the top view of FIG. 2A along the longitudinal direction of a resonator. FIG. 2C is a cross-sectional view as viewed by cutting vertically with respect to the substrate face and cutting vertically with respect to the longitudinal direction of the resonator in line IIC-IIC of the top view of FIG. 2A. The wavelength tunable semiconductor laser chip of FIG. 2A has a configuration of a DFB laser array type in which each part of four DFB lasers 201a to 201d, an optical multiplexer 203, and a semiconductor optical amplifier 204 is integrated onto an InP substrate. Each of the parts is connected via waveguides 202a, 202b. With reference to the cross-sectional view along the laser resonator of FIG. 2B, in a single DFB laser, a guide layer 213 having a diffraction grating 214 formed thereon is provided directly on an active layer 212 having an amplification action by injecting electric current. These layers 212, 213, and 214 are further sandwiched between an n-type InP clad layer 216 and a p-type InP clad layer 217.

Operation of laser oscillations occurs by grounding an n-side electrode 219, adding a positive voltage to a p-side electrode 220, and then injecting electric current to the active layer 212. At this time, since only a wavelength settled in a cycle of the diffraction grating 214 provides strong feedback, an oscillation of a single-mode is made in the vicinity of this wavelength. As shown in the cross-sectional view viewing the laser resonator of FIG. 2C in a light traveling direction, the single DFB laser has a so-called waveguide structure of an embedded type in which the periphery of the active layer 212 and guide layer 213 is embedded with the InP. An n-type InP current block layer 221 is provided to efficiently inject electric current into the active layer 212.

The optical multiplexer 203 is composed of a multi-mode interference-type waveguide with four inputs and one output. A transparent core layer 215 (corresponding to the waveguide 202a in FIG. 2A) of the waveguide formed continuously from the DFB laser is made of InGaAsP mixed crystal of a transparent composition for oscillation light. The semiconductor optical amplifier 204 is composed of a waveguide (the active layer) 212 having a gain identical to that of each of the DFB lasers 201a to 201d, but does not have the diffraction grating 214 formed thereon and is composed of a so-called Semiconductor Optical Amplifier (SOA). Incidentally, the specific structure, materials, and configuration parameters for each part of the above-described DFB laser are only exemplary, and as long as a semiconductor laser can be used as a laser light source applicable to a digital coherent communication scheme using multivalued phase amplitude modulation, the present invention is not limited to the above specific example.

In the wavelength tunable semiconductor laser chip 102, in order to prevent light emitted from the waveguide within the chip from being reflected on the end face of the chip, the waveguide is formed so as to be slightly tilted with respect to the end face of the chip instead of being vertical therewith. Further, on the end faces of the chip, antireflection coatings 211a, 211b are formed. A light output level can be adjusted by controlling the amount of current to be applied to the semiconductor optical amplifier 204. The diffraction gratings formed on the DFB lasers 201a to 201d of the DFB laser arrays are respectively formed in different pitches, and thus, it is operated such that they oscillate in different corresponding wavelengths, respectively. It is possible to change the wavelength of the output light by choosing one DFB laser, out of the DFB laser arrays, to be oscillated by applying current. In the present embodiment, an oscillation wavelength for each DFB laser array is set so as to have a wavelength interval of about 4 nm in a predetermined temperature in 1550 nm band. The oscillation wavelength of the DFB laser changes about 0.1 nm toward a longitudinal wavelength side when a chip temperature changes by one degree. Therefore, if the temperature of the laser is changed by 40 degrees from 20° C. to 60° C., the oscillation wavelength can be changed by 4 nm. Among oscillation wavelengths in each of the four DFB lasers 201a to 201d at a predetermined temperature, continuous changes to arbitrary wavelengths can be made. In the case of the configuration of the present embodiment in FIG. 2A to FIG. 2C, it is possible to make an oscillation with an arbitrary wavelength within the range of the wavelengths where 4×4 nm=16 nm. In FIG. 2A to FIG. 2C, the example of the array configuration including the four DFB lasers has been illustratively shown, but, if the number of DFB laser arrays is increased, a wavelength tunable range can further be broadened according to the number of arrays.

Figure 3:
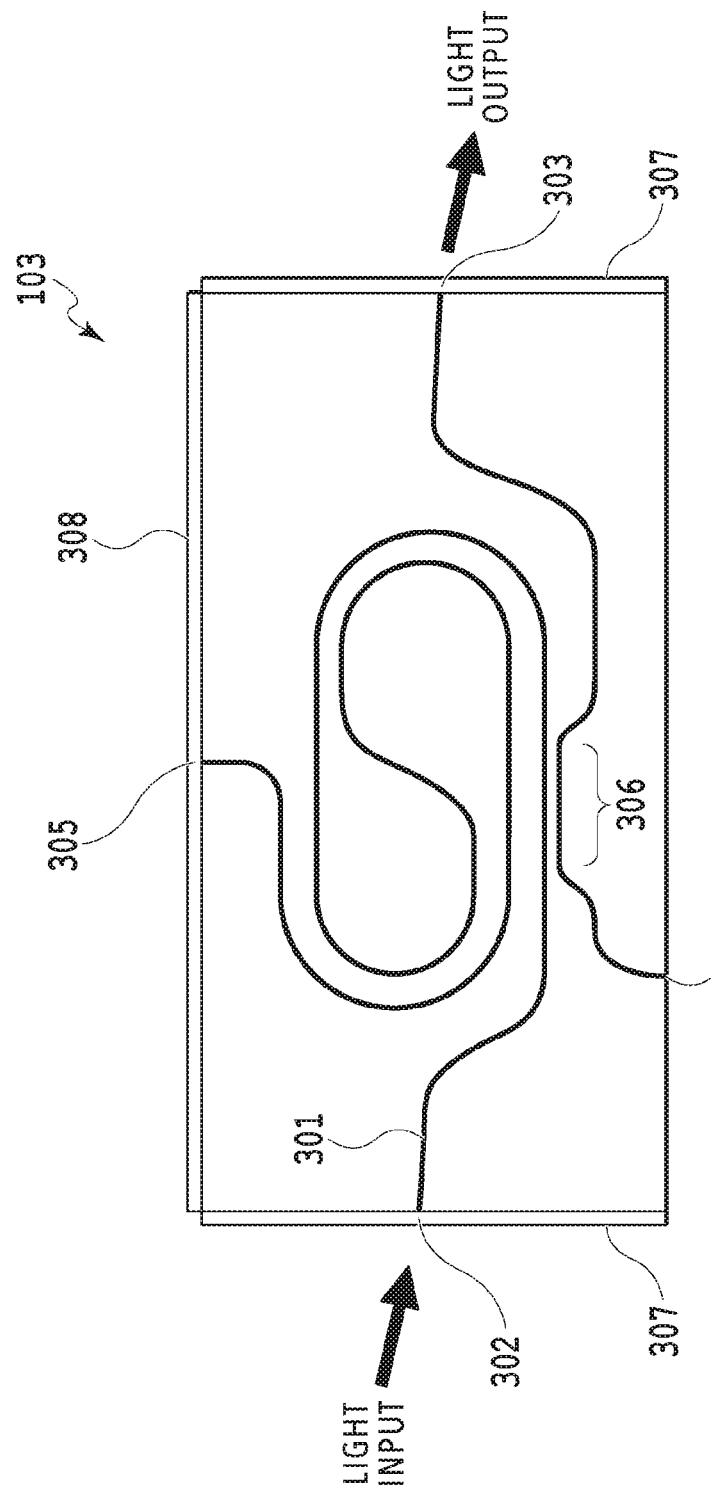
FIG. 3 is a diagram showing a more specific structure of a lightwave circuit chip for the semiconductor laser device of the present invention.

FIG. 3 is a diagram showing a more specific structure of the lightwave circuit chip for the semiconductor laser device of the present invention. The lightwave circuit 103 is fabricated by depositing SiO2 glass coating on a Si substrate. An optical waveguide 301 has a structure in which the periphery of a rectangular core layer having a high refractive index is embedded with a clad layer having a low refractive index. In the present embodiment, a refractive index difference between the core layer and the clad layer is about 2.5%. The oscillation light emitted from the wavelength tunable semiconductor laser chip 102 shown in FIG. 2A is entered into a light input part 302 of the optical waveguide 301 via the lenses 104, 105. The incident light propagates through the optical waveguide 301, and is divided, by a directional coupler 306, into a light propagating toward a light output part 303 and a light propagating toward a light reflector 305. The waveguide that guides part of the oscillation light toward the light reflector 305 is set so as to have its length of the optical path to belong to a certain extent. This is because the spectral linewidth is known to be narrowed in inverse proportion to the squared length of the optical path, and the effect of reducing the spectral linewidth is high in the case of extending the length of the optical path from the laser output part to the light reflector 305 to a certain extent. In order to make the spectral linewidth to 10 kHz or less, the length is required to be 10 cm or more, and preferably to be 40 to 50 cm or less for stable operation. In the optical waveguide 301 of the present embodiment, the length of the optical path from the light input part 302 to the light reflector 305 is set to be about 13 cm. Light reflected from the reflector 305 propagates through the optical waveguide in an inverse direction and returns to the light input part 302, and finally, is fed back to the semiconductor laser chip 102. Part of the reflected light propagates toward a light monitor output part 304 by the directional coupler 306.

In the light input part 302, the light output part 303, and the light monitor output part 304 in the lightwave circuit 103, optical waveguides are configured such that their propagation directions are tilted with respect to the end faces of the chip so as not to reflect the light at the end faces of the chip. Particularly, in the light input part 302 and the light output part 303, antireflective AR coatings 307a, 307b are formed on the respective end faces for suppressing the light reflection to be low. Meanwhile, in the light reflector 305, the optical waveguide is configured so as to be vertical with respect to the end face of the chip for obtaining a certain light reflection, and a high reflection coating 308 is coated on the surface of the reflector 305.

In the configuration example of the lightwave circuit chip of FIG. 3, an example including the reflector 305 on one end part of the chip for obtaining the reflected light has been presented, but the present invention is not necessarily limited to this configuration. For example, a loop-type reflector configured by combining a splitter and a waveguide on the lightwave circuit may be formed to reflect the oscillation light emitted from the wavelength tunable semiconductor laser chip 102 using the loop-type reflector.

Therefore, the semiconductor laser device of the present invention can be implemented as a semiconductor laser device comprising: a first substrate 102 having semiconductor lasers 201a to 201d formed thereon which oscillate in a single mode; a second substrate 103 having a lightwave circuit formed thereon which is configured to propagate part of output light from the semiconductor laser through a fixed length of an optical path and then to feed it back to the semiconductor laser; and a third substrate 101 having the first substrate and the second substrate mounted thereon, wherein output light from the semiconductor laser on the first substrate and an input waveguide of the lightwave circuit on the second substrate are optically connected to each other.

Preferably, the lightwave circuit may include a reflector 305 which reflects the propagated light and may be configured such that light reflected by the reflector is fed back to the semiconductor laser. Further preferably, the lightwave circuit on the second substrate may include branching means 306 for branching the output light from the semiconductor laser to generate the part of the output light.

Figure 4:
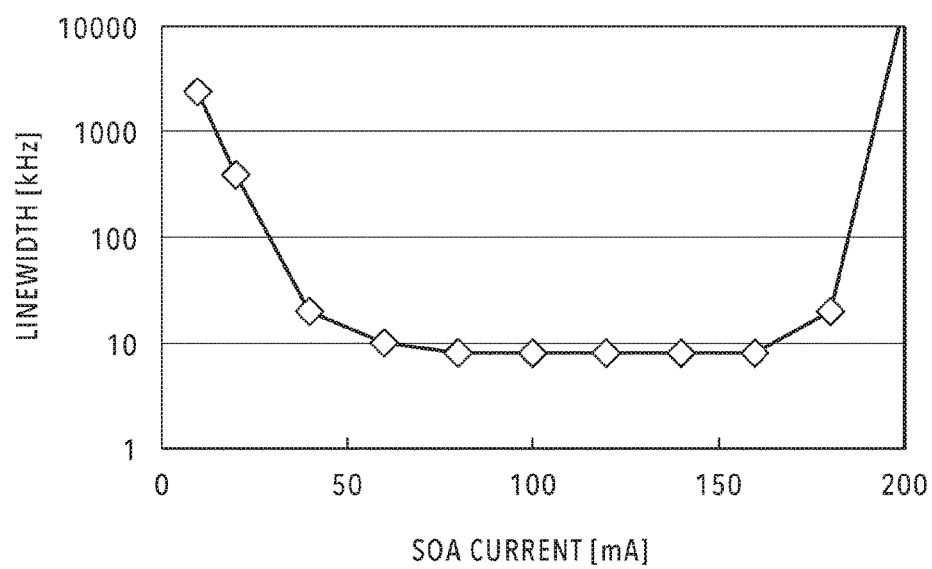
FIG. 4 is a diagram illustrating a characteristic of a spectral linewidth of the semiconductor laser device of the present invention.

FIG. 4 is a diagram illustrating a characteristic of the spectral linewidth of the semiconductor laser device of the present embodiment. FIG. 4 shows changes in the spectral linewidth in the case where the current of 150 mA has been injected into one laser out of the DFB laser arrays and values of the current to be applied to a semiconductor optical amplifier (SOA) 204 has been changed. At this time, the temperature of the semiconductor laser device 100 has been controlled to be 25° C. The spectral linewidth has been measured by using a time-delay self-heterodyne method. If SOA current is low, the amount of optical feedback to the DFB laser is small and thus the spectral linewidth is wide, but if the SOA current value is increased up to about 60 mA, the spectral linewidth is narrowed to 10 kHz or less. The spectral linewidth of the single DFB laser array has been about 2 to 3 MHz. According to the configuration of the semiconductor laser device of the present invention including the optical-feedback lightwave circuit, the spectral linewidth has been confirmed to be narrowed by more than two digits for the single DFB laser array. As shown in FIG. 4, when the SOA current value becomes 180 mA or more, the amount of optical feedback has become so large that the oscillation mode has been unstable, thereby rather increasing the spectral linewidth. Therefore, in the case of the configuration of the present embodiment, it is possible to stably operate the oscillation with the narrowed spectral linewidth when the SOA current value is used by around 100 mA.

In the present embodiment, as a structure of the semiconductor laser, the DFB structure in which the diffraction grating is formed on the waveguide having a gain has been explained as an example, but the structure of a Distributed Bragg Reflector (DBR) type formed on a waveguide in which a diffraction grating does not have a gain may be used. Also, instead of the laser arrays composed of the plurality of DFB lasers as shown in FIG. 2A to FIG. 2C, the present invention is applicable to a single DFB laser or DBR laser. Further, as a structure of the waveguide constituting the laser, the embedded type shown in FIG. 2C has been explained as an example, but the present invention is also applicable to a laser having a waveguide of a ridge type structure. The semiconductor laser device of the present invention can ensure stability of an operation environment of an optical feedback circuit by configuring an optical-feedback lightwave circuit using an optical waveguide free from deformation, and simultaneously, by arranging it on a substrate identical (common) to the substrate in which the semiconductor laser is configured. Therefore, as long as the optical feedback circuit is configured on a single substrate, the configuration of the feedback circuit also is not limited only to that of FIG. 3.

Further, in the configuration of the semiconductor laser device of the present invention shown in FIG. 1, the semiconductor laser chip 102 integrated onto the InP substrate has been explained as being directly mounted on the common substrate 101. However, the effect of the present invention can be similarly obtained as long as the two substrates are firmly fixed, and thus any method may be used for fixation between the two substrates 101 and 102. Moreover, the semiconductor laser chip 102 has been presented as one substrate in FIG. 1, but a chip including a semiconductor laser and other optical components and electric components may be mounted on another substrate, and such another substrate may be mounted on the common substrate 101.

Similarly, as for the lightwave circuit chip 103 as well, any method is allowable for fixation between the two substrates 101 and 103, which may include direct fixation and fixation by pinching some kind of material. Furthermore, a chip including a lightwave circuit and other optical components may be mounted on another substrate, and such another substrate may be mounted on the common substrate 101.

In the semiconductor laser device of the present embodiment, an optical-feedback lightwave circuit is configured by using an optical waveguide free from deformation and is arranged on a substrate identical to the one in which the semiconductor laser is held. Due to this, it is possible to ensure stability of an operation environment of the optical feedback circuit. In the optical feedback configuration of the semiconductor laser device of the present invention, the lightwave circuit does not have a function of a wavelength selective filter therein, but uses the wavelength tunable function included in the semiconductor laser. Due to this, as in the configuration of the external cavity laser, there is no need to make precise adjustment of wavelengths of the filter. The light source which is configured by combining the semiconductor laser chip and the lightwave circuit chip, which is small and has good wavelength controllability, and which has a narrowed spectral linewidth can be realized.

Second Embodiment

Figure 5:
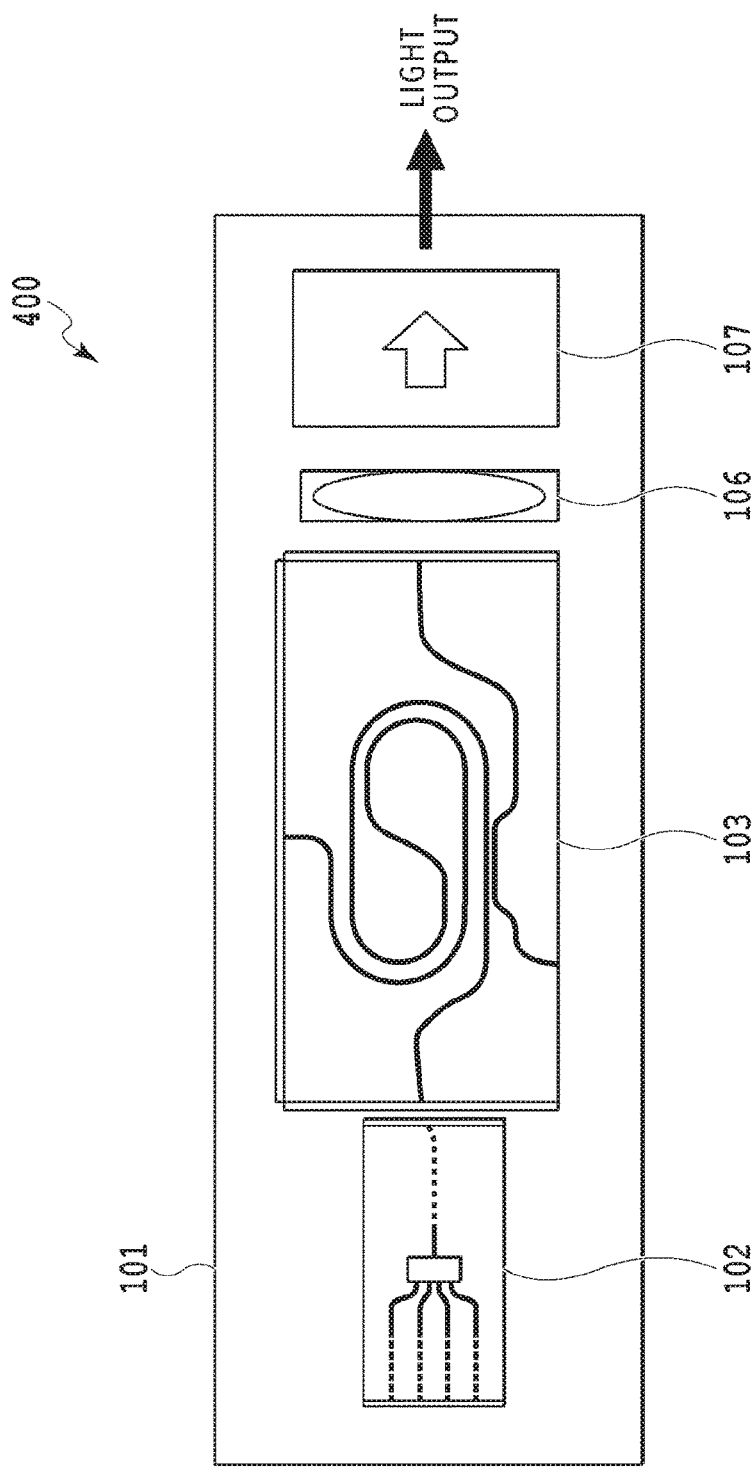
FIG. 5 is a diagram showing a rough sketch of the semiconductor laser device according to a second embodiment of the present invention.

FIG. 5 is a diagram showing a rough sketch of the semiconductor laser device according to the second embodiment of the present invention. When compared to the semiconductor laser device of the first embodiment, there are differences in that the semiconductor laser chip 102 and the lightwave circuit chip 103 are arranged so as to be in contact with each other and that output light from the semiconductor laser chip 102 is configured to be directly connected to the light input part of the lightwave circuit chip 103. As for the other configurations, they are identical to those of the first embodiment. In order to keep optical coupling efficiency high, each of the waveguides in the vicinities of the end parts of the chip is optimally configured so that an optical spot size of the light output part of the semiconductor laser chip 102 and an optical spot size of the light input part of the lightwave circuit chip 103 are as identical as possible. For example, an inclination angle of the waveguide in the end part of each chip is set so that the end faces of the chips can be directly connected to each other without reducing the optical coupling efficiency.

Therefore, the semiconductor laser device of the present embodiment can be carried out such that output light of the semiconductor laser on the first substrate 102 and an input waveguide 301 of the lightwave circuit on the second substrate 103 are connected to each other at the end face of the first substrate and the end face of the second substrate which face each other. In the configuration of the present embodiment, the semiconductor laser chip 102 and the lightwave circuit chip 103 need to be mounted on the substrate 101 with the precision of a submicron level. However, since the chips are optically connected directly without using the two lenses 104, 105 provided in the first embodiment, no area for mounting the lenses is needed, and thus, it is possible to achieve further downsizing of the semiconductor laser device.

In the semiconductor laser device of the present embodiment as well, as in the first embodiment, by injecting an appropriate current value into the SOA, it is possible to narrow the spectral linewidth by about two to three digits compared to the case of the single semiconductor laser. In the configuration of the semiconductor laser device of the present embodiment as well, the optical-feedback lightwave circuit is configured by using an optical waveguide free from deformation and is arranged on a substrate identical to the one in which the semiconductor laser is configured and held. Due to this, it is possible to ensure stability of an operation environment of the optical feedback circuit.

Incidentally, by providing a configuration in which an SOA chip further integrates with the lightwave circuit chip 103 and the lens 106 by forming it therebetween, it is possible to amplify light by the SOA so as to further increase a light output level.

Third Embodiment

In the above-described semiconductor laser devices of the first embodiment and second embodiment, oscillation light of the semiconductor laser chip and feedback light from the lightwave circuit chip both propagates through the common semiconductor optical amplifier (SOA) 204. Further, as explained in FIG. 4, the spectral linewidth has been controlled by changing the SOA current. In such a configuration, when determining an SOA current for the spectral linewidth, the output level of oscillation light also changes accordingly at the same time, and therefore, it is difficult to arbitrarily set the light output level from the semiconductor laser device. Hence, in the present embodiment, another configuration example that allows independent control of the light output level and the spectral linewidth while maintaining the effect of the present invention will be presented.

Figure 6:
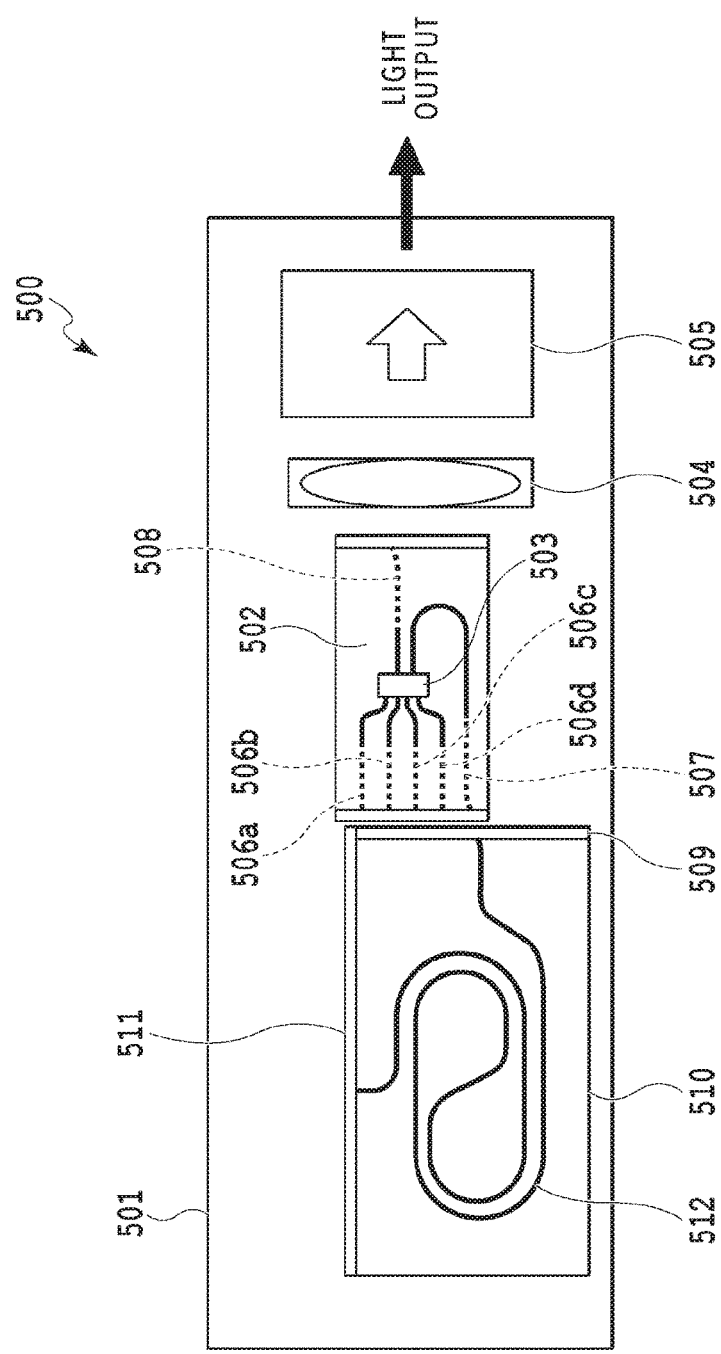
FIG. 6 is a diagram showing a rough sketch of the semiconductor laser device according to a third embodiment of the present invention.

FIG. 6 is a diagram showing a rough sketch of the semiconductor laser device according to the third embodiment of the present invention. A semiconductor laser device 500 of the present embodiment is similar to the configuration of the second embodiment in that a semiconductor laser chip 502 and a lightwave circuit chip 510 are also configured on a single substrate 501 and that the two chips are optically connected directly without having a lens therebetween. However, it is different from the configuration of the second embodiment in that multiplexed outputs of oscillation light from the semiconductor laser chip is divided into two routes, that is, an oscillation light output route and a feedback light route.

To be more specific, the semiconductor laser chip 502 of the present embodiment uses, for example, an optical multi/demultiplexer 503 of the four inputs and two outputs as an optical multiplexer that multiplexes oscillation lights from four DFB lasers 506a to 506d. The multi/demultiplexer 503 makes the output lights from the four DFB lasers branched into two routes, that is, a first route that outputs light to the outside as the output light of the semiconductor laser device via a first SOA 508 and a second route that outputs light to the lightwave circuit chip 510 via a second SOA 507. As such, in the present embodiment, it is different from the configuration of the second embodiment in that the output light is branched into two routes by the optical multi/demultiplexer 503 and each of the routes is provided with the individual SOA. The optical multi/demultiplexer 503 can be implemented by using a star coupler, a multi-mode interference-type optical multiplexer, or the like. The lightwave circuit chip 510 includes an optical reflector 511, an AR coating 509, an optical waveguide 512 of a predetermined length, which are identical to the configurations of the first embodiment and second embodiment.

Therefore, the present invention can be carried out as a semiconductor laser device comprising: a first substrate 502 having a semiconductor laser formed thereon which oscillates in a single mode; a second substrate 510 having a lightwave circuit formed thereon which is configured to propagate part of output light from the semiconductor laser through a fixed length of an optical path and then to feed it back to the semiconductor laser; and a third substrate 501 having the first substrate and the second substrate mounted thereon, wherein output light from the semiconductor laser on the first substrate and an input waveguide of the lightwave circuit on the second substrate are optically connected to each other, and wherein the first substrate includes: branching means 503 for branching the output light from the semiconductor laser into two, and generating the part of the output light of the second substrate as one branched light and generating output light of the semiconductor laser device as another branched light; and a first semiconductor optical amplifier 508 that amplifies the one branched light of the branching means and a second semiconductor optical amplifier 507 that amplifies the other branched light of the branching means.

As the four DFB lasers are configured in the third embodiment shown in FIG. 6, the optical multi/demultiplexer with the four inputs and two outputs is used as the optical multi/demultiplexer 503, but the present invention is not limited to this configuration. In other words, it is possible to employ an optical multi/demultiplexer with N inputs and two outputs in accordance with a number N of the DFB lasers. Alternatively, for monitoring a light output level, an optical multi/demultiplexer with three outputs may be employed. According to the configuration of the present embodiment, it is possible to set a light output level freely by independently controlling current to be applied to the first SOA 508 for light output while making current to be applied to the second SOA 507 for optical feedback to have an appropriate value that narrows the spectral linewidth. In the case where a branching circuit (directional coupler) is provided on the lightwave circuit chip side as in the first embodiment and the second embodiment, the output light of the semiconductor laser device is an output in which the part of the output of the SOA 204 is branched by the directional coupler 306, and therefore, the light output level takes a smaller value than the output of the SOA 204 at all times. In the configuration of the present embodiment, the output of the SOA 508 can be directly used as a light output of the light source. As a light source for communication, it is a great advantage that the light output level can be arbitrarily set. If the light output level is fixed as a light source, the scope of its application will be narrowed. As in the present embodiment, by adopting the configuration in which the multiplexed outputs are branched into two routes, it is possible to realize the light source that can flexibly set the spectral linewidth and the light output level. Incidentally, as also described in the second embodiment, the light output level can be adjusted by further integrating an SOA chip with the lightwave circuit chip 103 and the lens 106 by forming it therebetween. However, in this case, three chips are required for the entire semiconductor laser device, thereby inducing the increase in the cost of members and the cost for assembly, and therefore, the configuration of the present embodiment in which the output light from the semiconductor laser is branched into two, that is, the oscillation light output route and the feedback light route, is outstanding.

As specifically described above, according to the semiconductor laser device of the present invention, operation with the narrowed spectral linewidth can be made by returning the part of the output light of the semiconductor laser to the semiconductor laser by using the optical-feedback lightwave circuit. The light source which is configured by the combination of the semiconductor laser chip and the lightwave circuit chip, which is compact and has good controllability, and which has the narrowed spectral linewidth can be realized.

The present invention can be used for an optical communication system in general. In particular, the present invention can be used for a transmitter of the optical communication system, and further, can also be used for an optical sensing system.

The invention claimed is:

1. A semiconductor laser device comprising:
   a first substrate having a semiconductor laser formed thereon which oscillates in a single mode;
   a second substrate being composed of Si and having a lightwave circuit formed thereon which is configured to propagate part of output light from the semiconductor laser through a fixed length of an optical path and then to feed the part of output light back to the semiconductor laser; and
   a third substrate having the first substrate and the second substrate mounted thereon,
   wherein output light from the semiconductor laser on the first substrate and an input waveguide of the lightwave circuit on the second substrate are optically connected to each other, and wherein the first substrate includes:
   branching means for branching the output light from the semiconductor laser into two paths, and generating the part of the output light of the second substrate as one branched light and generating output light of the semiconductor laser device as another branched light; and
   a first semiconductor optical amplifier that amplifies the one branched light of the branching means and a second semiconductor optical amplifier that amplifies the other branched light of the branching means.

2. The semiconductor laser device according to claim 1, wherein the lightwave circuit on the second substrate includes a reflector which reflects the propagated light and is configured such that light reflected by the reflector is fed back to the semiconductor laser.

3. The semiconductor laser device according to claim 2, wherein the output light from the semiconductor laser on the first substrate and the input waveguide of the lightwave circuit on the second substrate are coupled between an end face of the first substrate and an end face of the second substrate that faces the end face of the first substrate.

4. The semiconductor laser device according to claim 2, wherein the semiconductor laser is a distributed feedback type (DFB) laser or a distributed reflection type (DBR) laser which includes a wavelength choosing function by a diffraction grating.

5. The semiconductor laser device according to claim 2, wherein the semiconductor laser includes a number N of distributed feedback type (DFB) laser arrays, an optical multiplexer configured so as to multiplex each of output lights from the number N of DFB laser arrays, and the semiconductor optical amplifiers, all integrated therein, and operates as a wavelength tunable laser.

6. The semiconductor laser device according to claim 2, wherein the semiconductor laser includes a number N of distributed reflection type (DBR) laser arrays, an optical multiplexer configured so as to multiplex each of output lights from the number N of DBR laser arrays, and the semiconductor optical amplifiers, all integrated therein, and operates as a wavelength tunable laser.

7. The semiconductor laser device according to claim 2, wherein the semiconductor laser includes a number N of laser arrays, an optical multiplexer configured so as to multiplex each of output lights from the number N of laser arrays, and the semiconductor optical amplifiers, all integrated therein, and operates as a wavelength tunable laser.

8. The semiconductor laser device according to claim 7, wherein the number N of laser arrays are any one of a number N of distributed feedback type (DFB) laser arrays or a number N of distributed reflection type (DBR) laser arrays.

9. The semiconductor laser device according to claim 1, wherein the output light from the semiconductor laser on the first substrate and the input waveguide of the lightwave circuit on the second substrate are coupled between an end face of the first substrate and an end face of the second substrate that faces the end face of the first substrate.

10. The semiconductor laser device according to claim 9, wherein the semiconductor laser is a distributed feedback type (DFB) laser or a distributed reflection type (DBR) laser which includes a wavelength choosing function by a diffraction grating.

11. The semiconductor laser device according to claim 1, wherein the semiconductor laser is a distributed feedback type (DFB) laser or a distributed reflection type (DBR) laser which includes a wavelength choosing function by a diffraction grating.

12. The semiconductor laser device according to claim 1, wherein the semiconductor laser includes a number N of distributed feedback type (DFB) laser arrays, an optical multiplexer configured so as to multiplex each of output lights from the number N of DFB laser arrays, and the semiconductor optical amplifiers, all integrated therein, and operates as a wavelength tunable laser.

13. The semiconductor laser device according to claim 1, wherein the semiconductor laser includes a number N of distributed reflection type (DBR) laser arrays, an optical multiplexer configured so as to multiplex each of output lights from the number N of DBR laser arrays, and the semiconductor optical amplifiers, all integrated therein, and operates as a wavelength tunable laser.

14. The semiconductor laser device according to claim 1, wherein the semiconductor laser includes a number N of laser arrays, an optical multiplexer configured so as to multiplex each of output lights from the number N of laser arrays, and the semiconductor optical amplifiers, all integrated therein, and operates as a wavelength tunable laser.

15. The semiconductor laser device according to claim 14, wherein the number N of laser arrays are any one of a number N of distributed feedback type (DFB) laser arrays or a number N of distributed reflection type (DBR) laser arrays.

* * * * *